(12) United States Patent
Neff et al.

(10) Patent No.: US 8,459,097 B2
(45) Date of Patent: Jun. 11, 2013

(54) METHOD AND CONTROL UNIT FOR DETECTING A GAS CONCENTRATION OF GAS FROM A GAS MIXTURE

(75) Inventors: Petra Neff, Stuttgart (DE); Markus Widenmeyer, Schoenaich (DE)

(73) Assignee: Robert Bosch GmbH, Stuttgart (DE)

( * ) Notice: Subject to any disclaimer, the term of this patent is extended or adjusted under 35 U.S.C. 154(b) by 387 days.

(21) Appl. No.: 12/927,945

(22) Filed: Nov. 29, 2010

(65) Prior Publication Data

US 2011/0138879 A1    Jun. 16, 2011

(30) Foreign Application Priority Data

Dec. 1, 2009   (DE) .......................... 10 2009 047 354

(51) Int. Cl.
    *G01N 7/00*    (2006.01)
(52) U.S. Cl.
    USPC .......................... 73/23.2; 73/23.31; 73/31.05
(58) Field of Classification Search
    USPC .............. 73/23.2, 23.31, 23.32, 23.33, 25.05; 340/632; 422/83; 204/424, 428
    See application file for complete search history.

(56) References Cited

U.S. PATENT DOCUMENTS

| | | | |
|---|---|---|---|
| 4,446,718 A * | 5/1984 | Bukowiecki et al. | ........ 73/31.06 |
| 4,703,646 A | 11/1987 | Müller et al. | |
| 5,683,569 A | 11/1997 | Chung et al. | |
| 5,889,196 A * | 3/1999 | Ueno et al. | ..................... 73/23.31 |
| 2003/0109056 A1 | 6/2003 | Vossmeyer et al. | |
| 2007/0278098 A1 | 12/2007 | Yokosawa et al. | |
| 2009/0272175 A1 | 11/2009 | Frerichs et al. | |

FOREIGN PATENT DOCUMENTS

WO    WO 02/082045    10/2002

* cited by examiner

*Primary Examiner* — John Fitzgerald
*Assistant Examiner* — Nathaniel Kolb
(74) *Attorney, Agent, or Firm* — Kenyon & Kenyon LLP

(57) ABSTRACT

A gas concentration of a gas may be detected from a gas mixture using gas detectors sensitive to the gas. A gas concentration may be measured by a first gas detector at a first operating temperature, and a first signal characteristic of the measured gas concentration may be provided. An operating temperature of the first gas detector may be changed to a second operating temperature, or a second gas detector having the second operating temperature may be provided. A gas concentration may then be measured at the second operating temperature, and a second signal characteristic of the measured gas concentration may be provided. The gas concentration of the gas from the gas mixture may be determined using a first concentration value allocated to the first signal and a second concentration value allocated to the second signal.

13 Claims, 3 Drawing Sheets

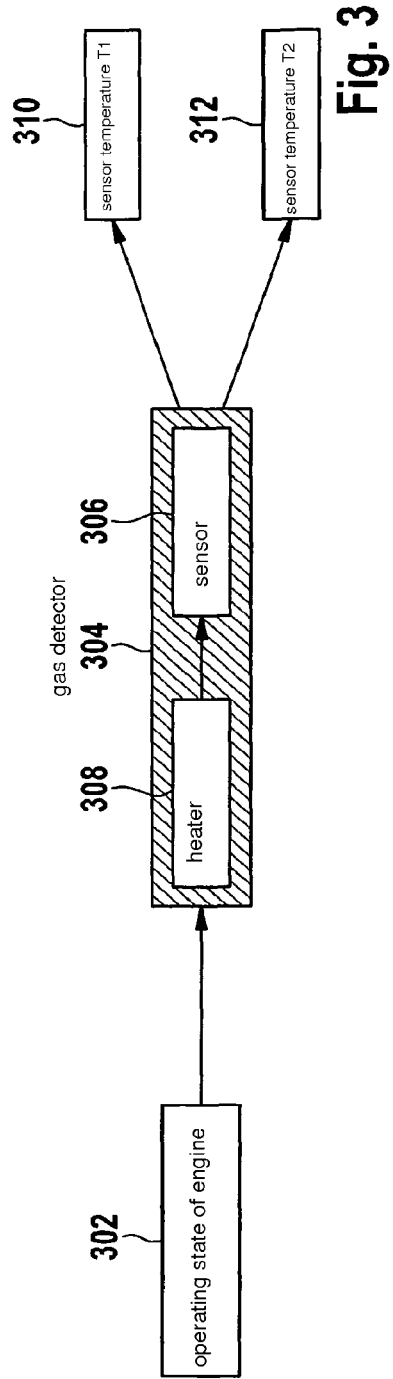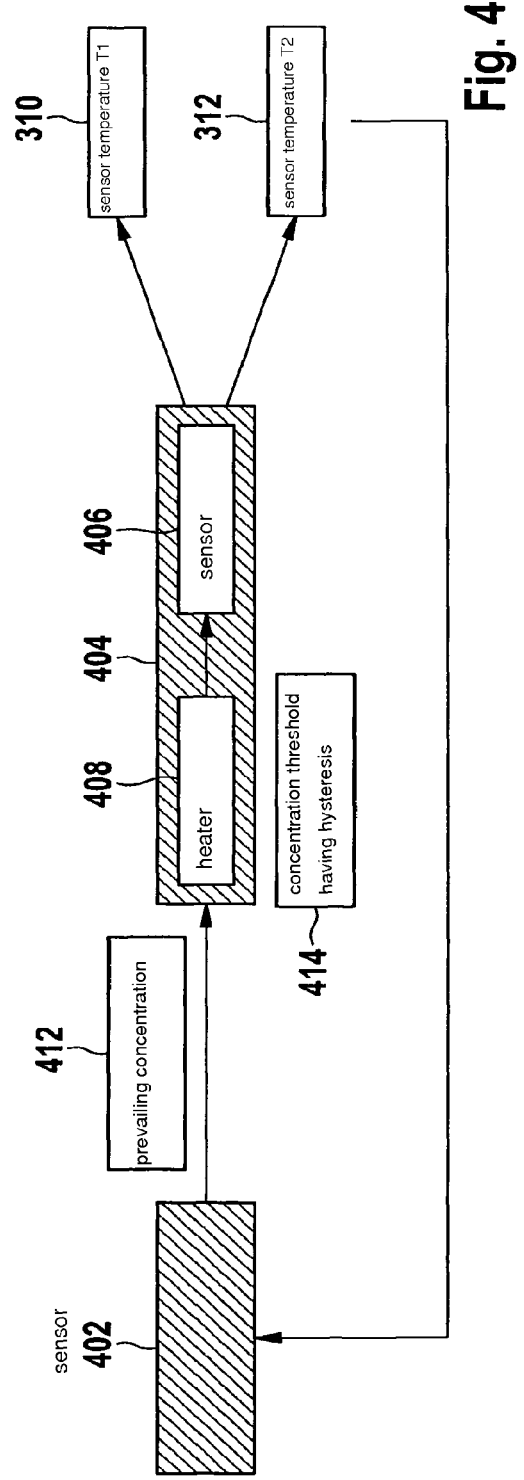

METHOD AND CONTROL UNIT FOR DETECTING A GAS CONCENTRATION OF GAS FROM A GAS MIXTURE

BACKGROUND OF THE INVENTION

1. Field of the Invention

The present invention relates to a method, a control unit, and a computer program product for detecting a gas concentration.

2. Description of the Related Art

Chemosensitive field-effect sensors are a novel technology for exhaust gas sensors, in particular for mobile exhaust gas sources. Because of the adsorptive measuring principle, the dependence of the measuring signal on the measured variable, which usually represents a concentration of a gas constituent, is sublinear rather than linear. This means, for example, that doubling the gas concentration of a certain analyte is not equivalent to doubling the measuring signal but instead only causes an increase by a smaller ratio. Based on the fact that the signal must have a certain intensity against a quasiconstant noise background, the result is that measuring certain changes in concentration, such as a change by 5 ppm in a certain gas species, is possible only up to a certain maximum concentration. At higher concentrations, only great changes in concentration by a few orders of magnitude are detectable. At even higher concentrations, the measuring signal may develop into saturation, i.e., a situation in which even a definite increase in the concentration to be measured no longer causes an increase in signal. The measurable concentration range may be shifted toward higher concentrations as a result of a change in the ambient conditions of the sensor, in particular by increasing the temperature of the sensor. The countereffect of the measure of raising the temperature is that the sensor loses precision in the range of low concentrations. In the case of mobile exhaust gas sources in particular, which may usually be operated under a wide range of different operating states, the widest possible measuring range over up to three orders of magnitude is desirable, for example, between 50 ppm and 5000 ppm, with a high measuring accuracy in the range of low concentrations at the same time.

US Patent Publication No. 2007/0278098 A1 describes a field-effect gas sensor which is based on a field-effect transistor and ensures a long operating time by minimizing the heat output. Two electrical lines are connected here to one gas-sensitive electrode, the gas-sensitive electrode being designed as a layer on the field-effect transistor, which acts as an insulating gate.

SUMMARY OF THE INVENTION

Against this background, the present invention provides a method as well as a control unit using this method and finally a corresponding computer program product according to the independent patent claims. Advantageous embodiments are derived from the respective subclaims and the following description.

The present invention creates a method for detecting a gas concentration of a gas from a gas mixture, a plurality of gas detectors, which are sensitive to the gas, or one gas detector, which is sensitive to the gas being used under different operating states, and the method including the following steps:

providing the gas detector, the gas detector having a first operating temperature;

supplying the gas mixture to the gas detector, a gas concentration of the gas from the gas mixture being measured by the gas detector at the first operating temperature, and a first signal characteristic of the measured gas concentration being provided;

changing the operating temperature of the gas detector to a second operating temperature, which is different from the first operating temperature, or providing another gas detector, the additional gas detector having the second operating temperature;

feeding the gas mixture to the gas detector or the additional gas detector, so that a gas concentration of the gas from the gas mixture is measured by the gas detector or the additional gas detector at the second operating temperature, and a second signal characteristic of the gas concentration to be measured is provided; and determining a gas concentration of the gas from the gas mixture using a first concentration value allocated to the first signal and a second concentration value allocated to the second signal.

The present invention also creates a control unit, which is designed to perform, i.e., implement, the steps of the method according to the present invention. Through this embodiment variant of the present invention in the form of a control unit, the object on which the present invention is based may also be achieved rapidly and efficiently.

A control unit in the present case may be understood to be an electrical device, which processes sensor signals and outputs control signals as a function thereof. The control unit may have an interface, which may be implemented in the form of hardware and/or software. In the case of hardware embodiment, the interfaces may be part of a so-called system ASIC, for example, which includes a wide variety of functions of the control unit. However, it is also possible for the interfaces to be dedicated integrated circuits or to have at least partially discrete components. In the case of software embodiment, the interfaces may be software modules, which are present on a microcontroller in addition to other software modules, for example.

Also advantageous is a computer program product having program code, which is stored on a machine-readable carrier, such as a semiconductor memory, a hard disk memory, or an optical memory and is used for performing the method according to one of the specific embodiments described above when the program is executed on a control unit.

The present invention is based on the finding that gas detectors have different sensitivities at different temperatures. To be able to perform the most accurate possible determination of the gas concentration of a gas in a gas mixture, the gas mixture is measured using a sensor or detector at different temperatures or using two detectors, which are operated at different temperatures. The range of magnitude of the concentration of the particular gas may then be classified approximately from the two measured values thereby obtained, so that for the further process sequence, the detector is used or operated at the temperature which ensures a more accurate concentration measurement of the gas in the concentration range according to the approximate classification. For example, if the gas concentration measured at the second operating temperature exceeds a threshold value, this measured gas concentration is output as a given gas concentration at the second operating temperature. However, if the measured gas concentration at the first operating temperature is below a (second) threshold value, the measured gas concentration may be output. In a particular specific embodiment of the present invention, a sensor system for mobile exhaust gas sources may be created, based on one or more field-effect chemosensors, so that one or more sensors are operated at a minimum of two different temperatures. The range in which measurements may be performed with a certain accuracy or concentration resolution is therefore enlarged.

The present invention offers the advantage of ensuring the widest possible measurable concentration range with a high measuring accuracy using technically simple means.

According to one specific embodiment of the present invention, the steps of providing, supplying, changing, feeding, and determining may be performed several times in succession. Such a specific embodiment of the present invention offers the advantage that additional concentration values may be detected for a single concentration value. The concentration values may be detected continuously to obtain additional information about an average concentration value from statistics about concentration values and in particular to calculate a range of variation relative to the average concentration value. This specific embodiment of the present invention additionally offers the advantage that concentration values may be compiled after certain intervals of time to detect a change in the concentration values during the interval of time, so that, for example, additional steps are executed when a concentration value exceeds a maximum limiting value.

Furthermore, according to another specific embodiment, in the step of providing and/or in the step of changing, the first and/or second operating temperature may be selected as a function of a temperature of an exhaust gas of an internal combustion engine. Such a specific embodiment of the present invention offers the advantage that the temperature of the exhaust gas, which is reached as the operating temperature of an exhaust gas purification system integrated into an exhaust gas duct, for example, may be defined as the value for the first operating temperature. A temperature of a heating element, which is in thermal contact with the gas detector or with the additional gas detector, may be used as the value for the second operating temperature, for example, the second operating temperature being kept constant by the heating element. Thus, during operation of the internal combustion engine, concentration values may also be detected at the (higher) temperature of the heating element.

In an additional specific embodiment, in the step of providing and/or in the step of changing, the first and the second operating temperature may be used, the first and second operating temperatures differing by at least 50K. Such a specific embodiment of the present invention offers the advantage that a measurement of a gas concentration is to be prevented if the first operating temperature is identical to or very similar in first approximation to the second operating temperature. A predefined temperature difference of 50K, for example, ensures an unambiguous determination of the gas concentration at sufficiently different operating temperatures, so that the different gas sensitivities of the gas detectors may be utilized.

According to another specific embodiment of the present invention, in the step of changing, the gas detector or the additional gas detector may have a second operating temperature, which is higher than the first operating temperature. In addition, in the step of determining, the first concentration value is output as the value for the gas concentration if the first and second concentration values are lower than a predetermined threshold value, in particular lower than 10 ppm. Furthermore in the step of determination, the second concentration value may be output if the first and second concentration values are higher than a predetermined threshold value, in particular higher than 10 ppm. Such a specific embodiment of the present invention offers the advantage that an operating temperature of the gas detector is selected as a function of the gas concentration at which the gas detector operates optimally and a deviation due to measurement error from a measured concentration value to an actual gas concentration is minimized. Therefore a high concentration resolution and a higher accuracy of the concentration value ascertained are achievable.

In an advantageous specific embodiment of the present invention, in the step of changing, the gas detector or the additional gas detector may have a second operating temperature which is higher than the first operating temperature. In the step of determining, the first concentration value may be output as the value for the gas concentration if the first concentration value is lower than a predefined upper concentration threshold value. Furthermore, in the step of determining, the second concentration value may be output if the second concentration value is higher than a predefined lower concentration threshold value, and the predefined upper concentration threshold value is higher than the predefined lower concentration threshold value. Such a specific embodiment of the present invention offers the advantage that a transitional range between the predefined lower concentration threshold value and the predefined upper concentration threshold values is defined so that within the transitional range, the gas detector or the additional gas detector may be operated either at the first or second operating temperature, depending on the concentration value measured in advance. Therefore, frequent changing between operation at the first or second operating temperature is avoidable in particular if the concentration value measured in advance is identical to either the upper or lower predefined concentration threshold value. Avoiding frequent switching of the operating temperature increases the lifetime of the gas sensor(s).

It is also advantageous if the method in the step of providing the gas detector and/or in the step of providing the additional gas detector provides a chemosensitive field-effect sensor as the gas detector and/or as the additional gas detector. Such a specific embodiment of the present invention offers the advantage that the chemosensitive field-effect sensor has gas-specific properties, in particular a high sensitivity at a low gas concentration and a high degree of adsorption at a low temperature. In addition, using the chemosensitive field-effect sensor, the concentration value is determined very easily with regard to the technology by using different physical variables, e.g., capacitance, conductance, or current.

Furthermore, according to a specific embodiment, in the step of determining, a step of allocating a signal to a concentration value may be performed. The allocating may be performed here using a predefined procedure of allocating signal values to concentration values. Such a specific embodiment of the present invention offers the advantage that a gas detector may be replaced easily if a measuring range is to be altered, for example. Complex reprogramming or rewiring of the measuring device may be omitted and instead one need only perform an exchange of the allocation table between the sensor signal and the corresponding measured value.

According to a favorable specific embodiment of the present invention, a step of measuring a gas concentration during at least one predefined period of time, in particular during at least 10 seconds, may also take place after the step of determining. The step of measuring a gas concentration may be performed as a function of the gas concentration determined (previously or formerly), using the gas detector either at the first operating temperature or at the second operating temperature or using the additional gas detector at the second operating temperature. Such a specific embodiment of the present invention offers the advantage that a measuring cycle may be performed using a gas detector selected during operation of the measuring method. In particular, either the gas detector may be used at the first operating temperature or the gas detector may be used at the second operating temperature or the additional gas detector may be used at the second operating temperature to determine the gas concentration with the required measuring accuracy. During the subsequent measuring cycle, there is neither a change between the first and second operating temperatures nor a change between the gas detector and the additional gas detector over a long period of time.

BRIEF DESCRIPTION OF THE DRAWINGS

The present invention will now be explained in greater detail on the basis of the accompanying drawings as an example.

FIG. 3 shows a flow chart of a method for ascertaining an operating temperature according to one exemplary embodiment of the present invention FIG. 4 shows another flow chart of a method for ascertaining an operating temperature according to one exemplary embodiment of the present invention.

DETAILED DESCRIPTION OF THE INVENTION

Figure 1:
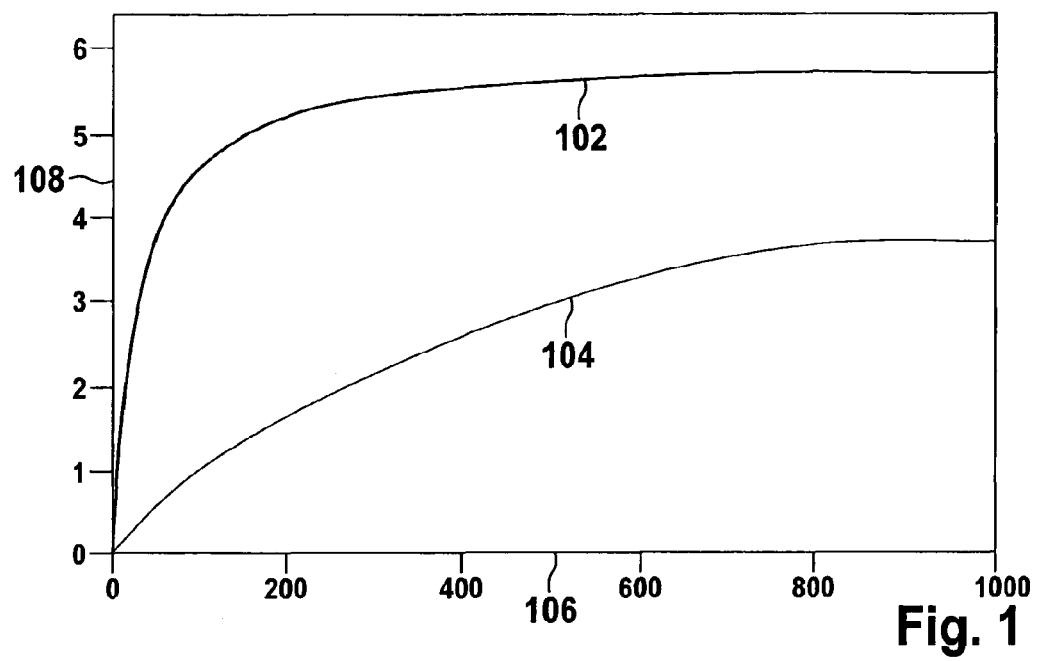
FIG. 1 shows a representation of an adsorption curve of a gas detector.

The same or similar elements may be provided with the same or similar reference numerals in the figures to avoid repeated description. Furthermore, the figures of the drawings, their description, and the claims contain numerous features in combination. It will be clear to those skilled in the art that these features may also be considered individually or may be combined into other combinations not described explicitly here. In addition, the present invention is explained in the following description using different measures and dimensions, but the present invention is not to be understood as limited to these measures and dimensions. Furthermore, method steps according to the present invention may be repeated and/or executed in a different order than that described here. If an exemplary embodiment includes an "and/or" link between a first feature/step and a second feature/step, then this may be read as the exemplary embodiment according to one specific embodiment including both the first feature/the first step and the second feature/the second step and according to another specific embodiment including either only the first feature/step or only the second feature/step.

FIG. 1 shows a graphic representation of a curve of a degree of adsorption 102, 104 as a function of a gas concentration at different temperatures. A horizontal axis (abscissa) 106 corresponds to the gas concentration of a gas from a gas mixture, and a vertical axis (ordinate) 108 corresponds to the degree of adsorption of the gas from the gas mixture. In particular, curve 102 shows the degree of adsorption at a low temperature, and curve 104 shows the degree of adsorption at a high temperature. Beyond a certain concentration value, the curve of the adsorption line at a low temperature develops into a saturation curve, but the curve of the degree of adsorption at a high temperature develops into a monotonic rise without entering the saturation phase. In particular, FIG. 1 thus shows a representation of adsorption behavior at two different temperatures.

Figure 2:
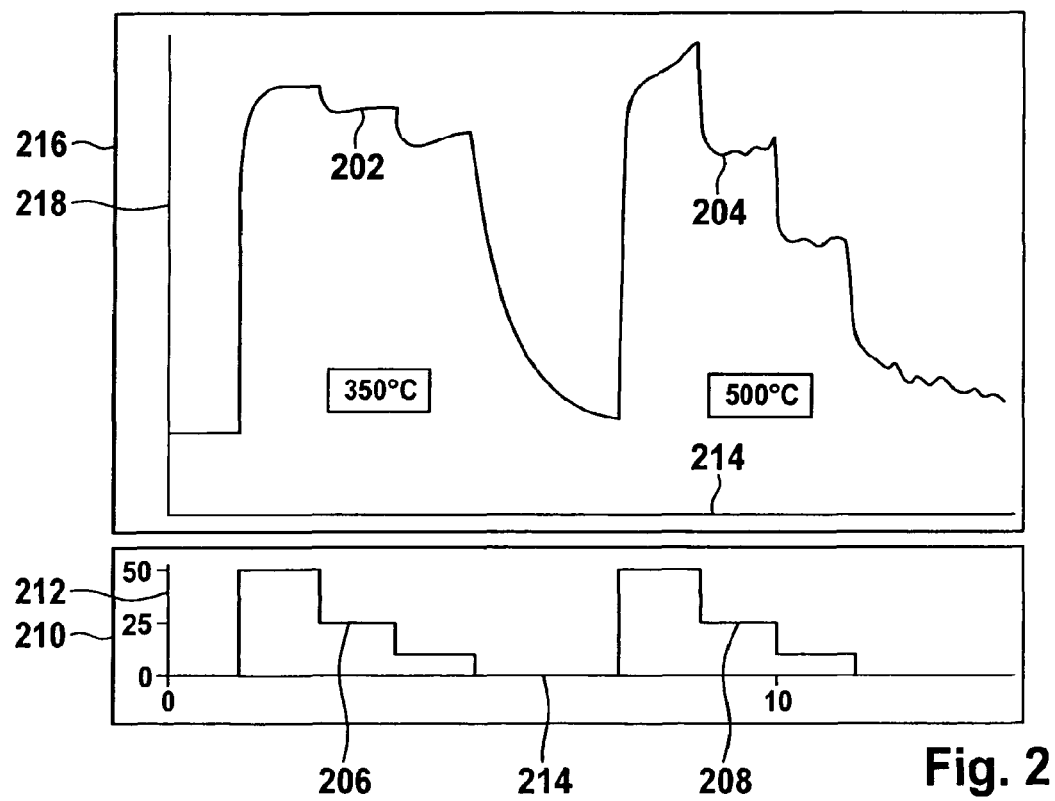
FIG. 2 shows a representation of a signal characteristic at the output of a gas detector.

FIG. 2 shows a graphic representation of an output signal 202, 204 of a gas detector as a function of time at different gas concentrations 206, 208 and at different temperatures. In a first diagram 210, a first curve 206 of gas concentration 212 of a gas from a gas mixture is plotted as a function of time 214 at a temperature of 350° C. In a second diagram 216, a first curve 202 for output signal 218 of the gas detector is plotted as a function of time, output signal 214 representing a characteristic variable of the gas detector as a function of concentration, temperature, and time. Similarly, a second curve 208 of gas concentration 212 of a gas from a gas mixture is plotted as a function of time 214 in a first diagram 210 for a temperature of 500° C., and a second curve 204 for output signal 218 of the gas detector as a function of time is shown in a second diagram 216. FIG. 2 shows a typical sensor response of a chemosensitive field-effect sensor at two different temperatures.

The characteristic response of chemosensitive field-effect sensors is greatly influenced by an adsorption equilibrium. The response of these sensors as a function of temperature and concentration may be explained in good approximation with the corresponding response of absorption equilibria. FIG. 1 shows in a theoretical model the adsorption response of an adsorptive, also known as an analyte, at two different temperatures. Two properties of the sensor are discernible, in particular a sublinearity as described above, and also the tendency to develop into saturation. In the specific case, the degree of this behavior depends greatly on temperature. At a low temperature, even low concentrations result in high degrees of adsorption. In contrast, there is hardly any discernible difference with regard to the degree of adsorption at certain concentration differences in the range of high concentrations. In other words, a saturation response occurs at even lower concentrations in comparison with higher temperatures. This behavior is also observed in real field-effect chemosensors, as shown in FIG. 2, and may be utilized with regard to expanding the measuring range. The exemplary representation in FIG. 2 shows that very low concentrations much below 10 ppm may be measured and resolved at 350° C. However, higher concentration values are much more difficult to differentiate from one another. In comparison, the measuring accuracy with regard to lower concentrations is reduced at 500° C. A higher measuring accuracy is much more pronounced at lower concentrations.

FIG. 3 shows a flow chart of a method for ascertaining an operating temperature of a gas detector. Possible elements for ascertaining the operating temperature include an engine operating state 302, a gas detector 304, gas detector 304 including a sensor 306 and a heater 308, which is in thermal contact with sensor 306, and gas detector 304 being capable of being operated in operating states at a first sensor temperature $T_1$ 310 and at a second sensor temperature $T_2$ 312.

According to one exemplary embodiment of the present invention, a chemosensor 306 (which is, for example, a special gas-sensitive field-effect transistor as the gas detector) may be operated at 350° C. or at 500° C., the corresponding measurement profiles 202, 204 being used as the basis for chemosensor 306, as shown in FIG. 2. If the exhaust gas purification system is in a state in which a concentration range of the type of gas to be measured of less than 10 ppm prevails, then operation occurs at 350° C.; otherwise operation occurs at 500° C. Thus concentration differences of at most 1 ppm may be measured below 10 ppm, and concentration differences of at most 5 ppm may be measured between 10 ppm and at least 50 ppm. Chemosensor 306 is therefore regulated either at a temperature of 350° C. or at a temperature of 500° C. For both temperature ranges, functions which allocate a concentration to the output signal of the sensor are stored in an electronic control and regulating device.

In contrast with FIG. 3, FIG. 4 shows a flow chart of a method for ascertaining an operating temperature of a gas detector using a defined concentration threshold. In addition to the elements for ascertaining the operating temperature, which were introduced in FIG. 3 as gas detector 304, sensor temperature $T_1$ 310 and sensor temperature $T_2$ 312, a sensor 406, a heater 408, another gas sensor 402, a prevailing concentration 412, and a concentration threshold having hysteresis 414 are required.

An implementation of a certain temperature range, for example, in the case of two different temperatures, may be provided as needed. Either the particular operating state of engine 302 is indicative of the temperature range in which the sensor is being operated, as shown in FIG. 3, or by comparison with a concentration threshold, the concentration measured instantaneously by the sensor indicates the temperature range in which the sensor is being operated, as shown in FIG. 4.

In another exemplary embodiment of the present invention, two chemosensors which are largely thermally uncoupled from one another may be used as an alternative. First sensor 406 is at a constant measurement temperature of 350° C., while second sensor 402 is at 500° C. Depending on the concentration range of the type of gas to be measured, optimum resolution of concentration differences may be achieved by using the first or second sensor. Functions which allocate a concentration to the output signal of the sensors are stored for both sensors. The operating state of the engine then indicates which sensor signal is to be processed further.

Figure 5:
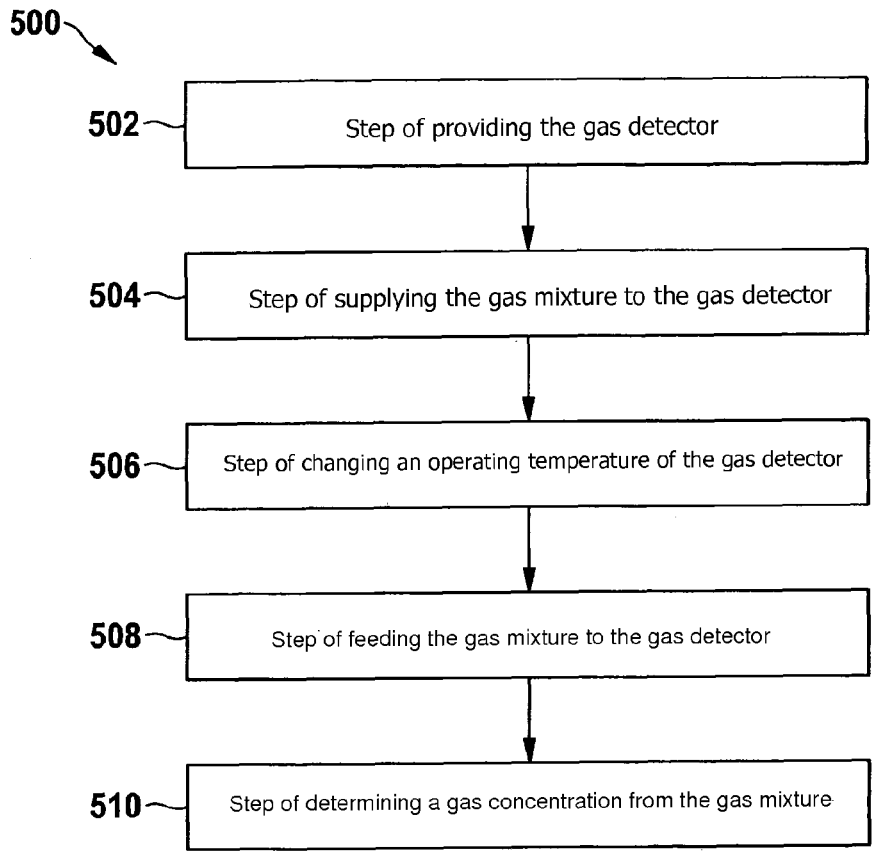
FIG. 5 shows a flow chart of a method for detecting a gas concentration according to one exemplary embodiment of the present invention.
Figure 6:
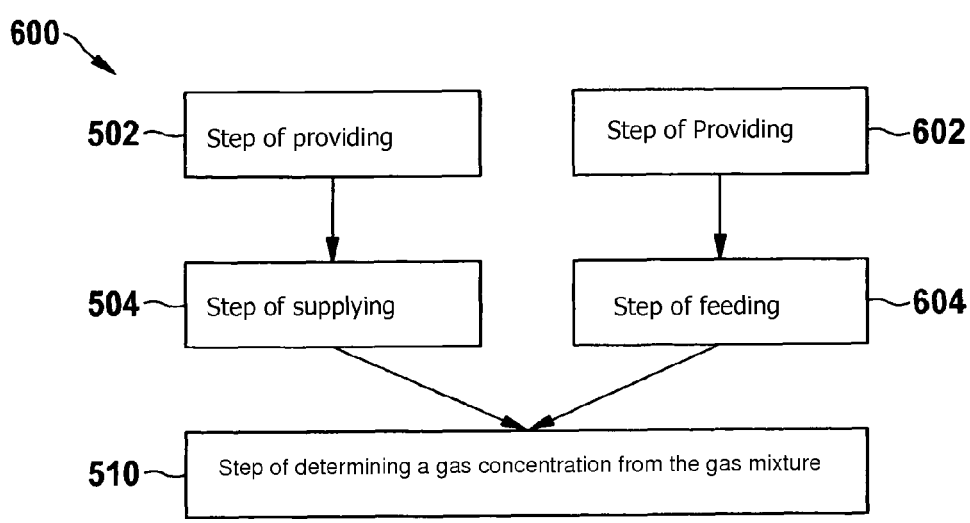
FIG. 6 shows another flow chart of a method for detecting a gas concentration according to one exemplary embodiment of the present invention.

In summary, it may be stated that the different temperatures are either implemented on one or more sensors in chronological order according to the present invention, as shown in FIG. 5, or they are implemented on at least two sensors, as shown in FIG. 6, for example. In the latter case, at least two individual sensors 306, 402 or thermally uncoupled chemosensitive field-effect sensors 306, 402 are necessary, individual sensors 306, 402 being operated at different temperatures, and the temperature being regulated at a constant level. If different temperatures are implemented in chronological order, these temperatures are implemented either periodically in succession, for example, in a temperature cycling pattern $T_1$-$T_2$-$T_1$-$T_2$, etc., or a certain temperature range is implemented, as needed, as shown in FIGS. 3 and 4. In this case, an engine and exhaust gas control or regulation specifies the temperature range to be implemented as a function of which concentration ranges are present in a certain operating situation 302, as shown in FIG. 3, or certain measuring powers are temporarily required on the basis of the concentration measured instantaneously, as shown in FIG. 4. In the case mentioned last, the instantaneous concentration is compared with a concentration threshold. A hysteresis in this concentration threshold may suppress cycling of the temperature range too often from the first operating temperature to the second and back again. The temperatures at which the measurements at the first and second operating temperatures are performed are advantageously in the range between 150° C. and 700° C. In addition, it is advantageous if two or more different (operating) temperatures are separated by at least 50K. An adequate gas sensitivity of the gas detector(s) at the different operating temperatures may be ensured in this way.

FIG. 5 shows a method 500 for detecting a gas concentration of a gas from a gas mixture according to one exemplary embodiment of the present invention. A plurality of gas detectors sensitive to the gas or one gas detector sensitive to the gas in different operating states may be used for detection. Method 500 in the case of a single gas detector is explained below. Method 500 includes a step of providing 502 the gas detector, so that the gas detector has a first operating temperature. In the step of supplying 504 the gas mixture to the gas detector, the gas detector is brought into contact with the gas mixture, so that a gas concentration of the gas from the gas mixture is measured by the gas detector at the first operating temperature, and a first signal which is characteristic of the measured gas concentration is supplied. Furthermore, method 500 includes a step of changing 506 an operating temperature of the gas detector to a second operating temperature, which is different from the first operating temperature. In the step of supplying the gas mixture to the gas detector, whereby a gas concentration of the gas from the gas mixture being measured by the gas detector at the second operating temperature, and a second signal which is characteristic of the measured gas concentration, is supplied. In addition, the method includes a step of determining a gas concentration of the gas from the gas mixture with the aid of a first concentration value allocated to the first signal and a second concentration value allocated to the second signal.

In contrast with FIG. 5, FIG. 6 shows a method 600 for detecting a gas concentration of a gas from a gas mixture according to an exemplary embodiment of the present invention. A plurality of gas detectors sensitive to the gas or one gas detector sensitive to the gas may be used in different operating states for this detection. Method 600 is described below in the case of two individual gas detectors. In parallel with the step of providing 502 and the step of supplying 504, a step of providing 602 another gas detector and a step of feeding 604 the gas mixture to the additional gas detector are performed here. In particular in the step of providing 602, another gas detector is provided, the additional gas detector having a second operating temperature. In a step of feeding 604 the gas mixture to the additional gas detector, a gas concentration of the gas from the gas mixture is measured by the additional gas detector at the second operating temperature and a second signal characteristic of the measured gas concentration is provided.

What is claimed is:

1. A method for detecting a gas concentration of a gas from a gas mixture using a plurality of gas detectors which are sensitive to the gas or using one gas detector which is sensitive to the gas in different operating states, the method comprising:

providing the gas detector, the gas detector having a first operating temperature;

supplying the gas mixture to the gas detector, a gas concentration of the gas from the gas mixture being measured by the gas detector at the first operating temperature, and generating a first signal, which is characteristic of the measured gas concentration;

changing an operating temperature of the gas detector to a second operating temperature, which is higher than the first operating temperature, or providing an additional gas detector, the additional gas detector having the second operating temperature;

feeding the gas mixture to the gas detector or the additional gas detector, a gas concentration of the gas from the gas mixture being measured by the gas detector or the additional gas detector at the second operating temperature, and generating a second signal, which is characteristic of the measured gas concentration; and determining a gas concentration of the gas from the gas mixture using a first concentration value allocated to the first signal and a second concentration value allocated to the second signal, wherein the first concentration value is output as a value for the gas concentration when the first concentration value is lower than a predefined upper concentration threshold value and the second concentration value is output when the second concentration value is higher than a predefined lower concentration threshold value, the predefined upper concentration threshold value being higher than the predefined lower concentration threshold value.

2. The method as recited in claim 1, wherein the steps of providing, supplying, changing, feeding and determining are executed a plurality of times in succession.

3. The method as recited in claim 2, wherein at least one of the first and the second operating temperature is selected as a function of an operating state of an internal combustion engine in at least one of the step of providing and the step of changing.

4. The method as recited in claim 2, wherein the first and the second operating temperatures, which differ by at least 50K, are used in at least one of the step of providing and the step of changing.

5. The method as recited in claim 1, wherein at least one of the first and the second operating temperature is selected as a function of an operating state of an internal combustion engine in at least one of the step of providing and the step of changing.

6. The method as recited in claim 5, wherein the first and the second operating temperatures, which differ by at least 50K, are used in at least one of the step of providing and the step of changing.

7. The method as recited in claim 1, wherein the first and the second operating temperatures, which differ by at least 50K, are used in at least one of the step of providing and the step of changing.

8. The method as recited in claim 1, wherein each threshold value is 10 ppm.

9. The method as recited in claim 1, wherein a chemosensitive field-effect sensor is provided as the gas detector or the additional gas detector in at least one of the step of providing the gas detector and the step of providing the additional gas detector.

10. The method as recited in claim 1, wherein in the step of determining, a step of allocating a signal to a concentration value is performed, the allocation taking place using a predefined allocation procedure of signals to concentration values.

11. The method as recited in claim 1, wherein after the step of determining, a step of a measuring a gas concentration during at least one predefined period of time is additionally performed, the step of measuring a gas concentration being executed either using the gas detector at the first operating temperature or using the gas detector at the second operating temperature or the additional gas detector at the second operating temperature, as a function of the certain gas concentration determined previously or in advance.

12. The method according to claim 11, wherein the predefined period of time is at least 10 seconds.

13. A computer program product having program code, which is stored on a non-transitory machine-readable carrier, for performing the method as recited in claim 1, when the program is executed on a control unit.

\* \* \* \* \*